(12) United States Patent
Wilson et al.

(10) Patent No.: US 11,638,651 B2
(45) Date of Patent: May 2, 2023

(54) SPINAL IMPLANT (71) Applicant: K2M, Inc., Leesburg, VA (US)

(72) Inventors: Lester Wilson, Middlesex (GB);
Thomas Morrison, Atlanta, GA (US);
Hilali Noordeen, London (GB);
Jennifer Moore, Leesburg, VA (US);
Clint Boyd, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 344 days.

(21) Appl. No.: 16/850,195

(22) Filed: Apr. 16, 2020

(65) Prior Publication Data
US 2020/0237526 A1 Jul. 30, 2020

Related U.S. Application Data (63) Continuation of application No. 15/007,678, filed on Jan. 27, 2016, now Pat. No. 10,660,763.
(Continued)

(51) Int. Cl.
*A61F 2/44* (2006.01)
*A61B 17/70* (2006.01)
(Continued)

(52) U.S. Cl.
CPC ........ *A61F 2/4455* (2013.01); *A61B 17/7059* (2013.01); *A61B 17/8625* (2013.01);
(Continued)

(58) Field of Classification Search
CPC ...... A61F 2/4455; A61F 2/446; A61F 2/4465; A61F 2/447
See application file for complete search history.

(56) References Cited

U.S. PATENT DOCUMENTS 5,534,031 A   7/1996 Matsuzaki et al.
5,595,703 A   1/1997 Swaelens et al.
(Continued)

FOREIGN PATENT DOCUMENTS

CN   103445883 A   12/2013
DE   102008024281 A1   12/2009
(Continued)

OTHER PUBLICATIONS

Akamaru et al., Healing of Autologous Bone in a Titanium Mesh Cage Used in Anterior Column Reconstruction After Total Spondylectomy; SPINE vol. 27, No. 13, pp. E329-E333, Jan. 2002.
(Continued)

*Primary Examiner* — Matthew J Lawson
(74) *Attorney, Agent, or Firm* — Lerner David LLP (57) ABSTRACT

A spinal implant is provided and includes a body portion defining a longitudinal axis. The body portion includes a distal end portion, a proximal end portion, opposed side surfaces that extend between the distal and proximal end portions, and top and bottom surfaces configured and adapted to engage vertebral bodies. The top and bottom surfaces have a surface roughness between 3-4 μm. A cavity extends through the top and bottom surfaces defining a surface area that is at least 25% of a surface area of the top surface or the bottom surface. First orifices are defined through the top surface and second orifices are defined through the bottom surface. The second orifices are connected to the first orifices by a plurality of channel.

20 Claims, 10 Drawing Sheets

Related U.S. Application Data (60) Provisional application No. 62/196,371, filed on Jul. 24, 2015, provisional application No. 62/108,197, filed on Jan. 27, 2015.

(51) Int. Cl.
*A61B 17/86* (2006.01)
*A61F 2/30* (2006.01)

(52) U.S. Cl.
CPC .............. *A61F 2/44* (2013.01); *A61F 2/447* (2013.01); *A61F 2/4465* (2013.01); *A61F 2002/3092* (2013.01); *A61F 2002/3093* (2013.01); *A61F 2002/30593* (2013.01); *A61F 2002/30622* (2013.01); *A61F 2002/30784* (2013.01); *A61F 2002/30904* (2013.01); *A61F 2310/00023* (2013.01)

(56) References Cited

U.S. PATENT DOCUMENTS

| | | | |
|---|---|---|---|
| 5,609,635 A * | 3/1997 | Michelson | A61F 2/442 606/907 |
| 5,634,926 A | 6/1997 | Jobe | |
| 5,702,449 A | 12/1997 | McKay | |
| 5,733,286 A | 3/1998 | Errico et al. | |
| 5,768,134 A | 6/1998 | Swaelens et al. | |
| 5,786,134 A | 7/1998 | Nair et al. | |
| 5,888,227 A * | 3/1999 | Cottle | A61F 2/442 623/17.16 |
| 5,943,235 A | 8/1999 | Earl et al. | |
| 5,968,098 A | 10/1999 | Winslow | |
| 6,010,502 A | 1/2000 | Bagby | |
| 6,039,762 A | 3/2000 | McKay | |
| 6,129,730 A | 10/2000 | Bono et al. | |
| 6,342,055 B1 | 1/2002 | Eisermann et al. | |
| 6,391,058 B1 | 5/2002 | Kuslich et al. | |
| 6,432,107 B1 | 8/2002 | Ferree | |
| 6,520,996 B1 | 2/2003 | Manasas et al. | |
| 6,530,955 B2 | 3/2003 | Boyle et al. | |
| 6,530,956 B1 * | 3/2003 | Mansmann | A61F 2/38 623/18.11 |
| 6,716,247 B2 | 4/2004 | Michelson | |
| 6,730,127 B2 | 5/2004 | Michelson | |
| 6,758,849 B1 | 7/2004 | Michelson | |
| 6,855,167 B2 | 2/2005 | Shimp et al. | |
| 7,238,206 B2 | 7/2007 | Lange et al. | |
| 7,442,209 B2 * | 10/2008 | Michelson | A61F 2/4611 623/17.11 |
| 7,509,183 B2 | 3/2009 | Lin et al. | |
| 7,665,979 B2 | 2/2010 | Heugel | |
| 7,806,911 B2 | 10/2010 | Peckham | |
| 7,815,682 B1 * | 10/2010 | Peterson | A61F 2/4465 623/17.16 |
| 7,909,872 B2 | 3/2011 | Zipnick et al. | |
| D664,252 S | 7/2012 | Weiland et al. | |
| 8,275,594 B2 | 9/2012 | Lin et al. | |
| 8,287,541 B2 | 10/2012 | Nelson et al. | |
| 8,403,986 B2 | 3/2013 | Michelson | |
| 8,439,977 B2 | 5/2013 | Kostuik et al. | |
| 8,449,585 B2 | 5/2013 | Wallenstein et al. | |
| 8,585,761 B2 | 11/2013 | Theofilos | |
| 8,590,157 B2 | 11/2013 | Kruth et al. | |
| 8,669,043 B2 | 3/2014 | Mills et al. | |
| 8,673,011 B2 | 3/2014 | Theofilos et al. | |
| 8,697,231 B2 | 4/2014 | Longepied et al. | |
| 8,784,721 B2 | 7/2014 | Philippi et al. | |
| 8,801,791 B2 | 8/2014 | Soo et al. | |
| 8,814,919 B2 | 8/2014 | Barrus et al. | |
| 8,843,229 B2 | 9/2014 | Vanasse et al. | |
| 8,870,957 B2 | 10/2014 | Vraney et al. | |
| 8,903,533 B2 | 12/2014 | Eggers et al. | |
| 8,932,356 B2 | 1/2015 | Kraus | |
| 8,967,990 B2 | 3/2015 | Weidinger et al. | |
| 8,999,711 B2 | 4/2015 | Harlow et al. | |
| 9,011,982 B2 | 4/2015 | Muller et al. | |
| 9,283,078 B2 | 3/2016 | Roels et al. | |
| D786,434 S | 5/2017 | Trautwein | |
| 9,700,431 B2 | 7/2017 | Nebosky et al. | |
| 9,931,148 B2 | 4/2018 | Grady, Jr. et al. | |
| 10,716,678 B2 * | 7/2020 | Stampfli | A61F 2/442 |
| 2001/0047207 A1 | 11/2001 | Michelson | |
| 2001/0047208 A1 | 11/2001 | Michelson | |
| 2002/0128714 A1 | 9/2002 | Manasas et al. | |
| 2003/0040798 A1 | 2/2003 | Michelson | |
| 2003/0135276 A1 | 7/2003 | Eckman | |
| 2004/0024400 A1 | 2/2004 | Michelson | |
| 2004/0034352 A1 | 2/2004 | Needham et al. | |
| 2004/0243237 A1 | 12/2004 | Unwin et al. | |
| 2004/0249471 A1 | 12/2004 | Bindseil et al. | |
| 2005/0010226 A1 | 1/2005 | Grady et al. | |
| 2005/0021151 A1 | 1/2005 | Landis | |
| 2005/0112397 A1 | 5/2005 | Rolfe et al. | |
| 2005/0137597 A1 | 6/2005 | Butler et al. | |
| 2005/0149192 A1 | 7/2005 | Zucherman et al. | |
| 2005/0165400 A1 | 7/2005 | Fernandez | |
| 2005/0177238 A1 | 8/2005 | Khandkar et al. | |
| 2005/0246021 A1 | 11/2005 | Ringeisen et al. | |
| 2006/0173542 A1 * | 8/2006 | Shikinami | A61F 2/30965 623/17.16 |
| 2006/0235403 A1 | 10/2006 | Blain | |
| 2006/0264946 A1 | 11/2006 | Young | |
| 2007/0179610 A1 * | 8/2007 | Biedermann | G02F 1/13439 623/16.11 |
| 2007/0233272 A1 | 10/2007 | Boyce et al. | |
| 2007/0260324 A1 | 11/2007 | Joshi et al. | |
| 2007/0270812 A1 | 11/2007 | Peckham | |
| 2007/0270965 A1 | 11/2007 | Ferguson | |
| 2008/0097444 A1 | 4/2008 | Erickson et al. | |
| 2009/0018584 A1 | 1/2009 | Henderson, Sr. et al. | |
| 2009/0048675 A1 | 2/2009 | Bhatnagar et al. | |
| 2009/0054930 A1 | 2/2009 | Aflatoon | |
| 2009/0093881 A1 | 4/2009 | Bandyopadhyay et al. | |
| 2009/0270986 A1 | 10/2009 | Christensen | |
| 2009/0291308 A1 | 11/2009 | Pfister et al. | |
| 2009/0295042 A1 | 12/2009 | Pfister et al. | |
| 2010/0004747 A1 | 1/2010 | Lin | |
| 2010/0100131 A1 | 4/2010 | Wallenstein | |
| 2010/0137990 A1 | 6/2010 | Apatsidis et al. | |
| 2010/0228369 A1 | 9/2010 | Eggers et al. | |
| 2010/0234966 A1 | 9/2010 | Lo | |
| 2010/0268339 A1 | 10/2010 | Malinin et al. | |
| 2011/0144752 A1 | 6/2011 | Defelice et al. | |
| 2011/0165340 A1 | 7/2011 | Baumann | |
| 2011/0168091 A1 | 7/2011 | Baumann et al. | |
| 2011/0190888 A1 | 8/2011 | Bertele et al. | |
| 2011/0190904 A1 | 8/2011 | Lechmann et al. | |
| 2011/0301709 A1 | 12/2011 | Kraus et al. | |
| 2012/0046750 A1 | 2/2012 | Obrigkeit et al. | |
| 2012/0143334 A1 | 6/2012 | Boyce et al. | |
| 2012/0158062 A1 | 6/2012 | Nunley et al. | |
| 2012/0179261 A1 | 7/2012 | Soo | |
| 2012/0191188 A1 * | 7/2012 | Huang | A61F 2/447 623/17.11 |
| 2012/0191189 A1 | 7/2012 | Huang | |
| 2012/0203229 A1 | 8/2012 | Appenzeller et al. | |
| 2012/0303128 A1 | 11/2012 | Ullrich, Jr. et al. | |
| 2012/0310364 A1 | 12/2012 | Li et al. | |
| 2012/0316650 A1 | 12/2012 | Ullrich, Jr. et al. | |
| 2013/0046345 A1 | 2/2013 | Jones et al. | |
| 2013/0110243 A1 | 5/2013 | Patterson et al. | |
| 2013/0116793 A1 * | 5/2013 | Kloss | A61F 2/442 623/17.16 |
| 2013/0171019 A1 | 7/2013 | Gessler et al. | |
| 2013/0184765 A1 | 7/2013 | Beyar et al. | |
| 2013/0273131 A1 | 10/2013 | Frangov et al. | |
| 2014/0088716 A1 | 3/2014 | Zubok et al. | |
| 2014/0107785 A1 | 4/2014 | Geisler et al. | |
| 2014/0107786 A1 | 4/2014 | Geisler et al. | |
| 2014/0172111 A1 | 6/2014 | Lang et al. | |
| 2015/0018956 A1 | 1/2015 | Steinmann et al. | |
| 2015/0045924 A1 | 2/2015 | Cluckers et al. | |
| 2015/0134063 A1 | 5/2015 | Steinmann et al. | |

(56) References Cited

U.S. PATENT DOCUMENTS

| | | | |
|---|---|---|---|
| 2015/0142158 A1 | 5/2015 | Szwedka | |
| 2015/0367575 A1 | 12/2015 | Roels et al. | |
| 2016/0022431 A1* | 1/2016 | Wickham | A61F 2/447 623/17.16 |
| 2016/0030188 A1* | 2/2016 | Lynn | A61F 2/30744 623/17.16 |
| 2016/0038301 A1 | 2/2016 | Wickham | |
| 2016/0058575 A1 | 3/2016 | Sutterlin, III et al. | |
| 2016/0213485 A1 | 7/2016 | Schaufler et al. | |
| 2016/0213486 A1 | 7/2016 | Nunley et al. | |
| 2016/0213487 A1 | 7/2016 | Wilson et al. | |
| 2016/0213488 A1 | 7/2016 | Moore et al. | |
| 2019/0298542 A1 | 10/2019 | Kloss | |
| 2019/0328546 A1 | 10/2019 | Palagi et al. | |

FOREIGN PATENT DOCUMENTS

| | | |
|---|---|---|
| DE | 102008024288 A1 | 12/2009 |
| EP | 0425542 B1 | 3/1995 |
| EP | 1464307 A1 | 10/2004 |
| EP | 1905391 B1 | 1/2010 |
| EP | 2145913 A1 | 1/2010 |
| EP | 2457538 A1 | 5/2012 |
| EP | 1772108 B1 | 11/2015 |
| WO | 9000037 A1 | 1/1990 |
| WO | 9405235 A1 | 3/1994 |
| WO | 9419174 A1 | 9/1994 |
| WO | 9510248 A1 | 4/1995 |
| WO | 9532673 A1 | 12/1995 |
| WO | 9608360 A1 | 3/1996 |
| WO | 9628117 A1 | 9/1996 |
| WO | 9640015 A1 | 12/1996 |
| WO | 9640019 A1 | 12/1996 |
| WO | 9734546 A1 | 9/1997 |
| WO | 0025707 A1 | 5/2000 |
| WO | 0040177 A1 | 7/2000 |
| WO | 0066045 A1 | 11/2000 |
| WO | 0202151 A2 | 1/2002 |
| WO | 0230337 A2 | 4/2002 |
| WO | 02080820 A1 | 10/2002 |
| WO | 2006101837 A2 | 9/2006 |
| WO | 2009068021 A1 | 6/2009 |
| WO | 2011030017 A1 | 3/2011 |
| WO | 201317647 A1 | 2/2013 |
| WO | 2013155500 A1 | 10/2013 |
| WO | 2013156545 A1 | 10/2013 |
| WO | 201496294 A1 | 6/2014 |

OTHER PUBLICATIONS

Australian Examination Report for Application No. 2016200443 dated Sep. 11, 2019, 4 pages.

Bridwell et al., Specialty Update, What's New in Spine Surgery, The Journal of Bone and Joint Surgery, Incorporated, pp. 1022-1030, Core 1st page of article, Jun. 2015.

Cheung et al., Spinal Instrumentation Overview in Lumbar Degenerative Disorders: Cages, Lumbar Spine: Official Publication of the International Society for the Study of Lumbar Spine (3), pp. 286-291, 2004.

Chong et al., The design evolution of interbody cages in anterior cervical discectomy and fusion: a systematic review BMC Musculoskeletal Disorders Apr. 2015 16:99, pp. 1-20.

Costa et al., Stand-alone cage for posterior lumbar interbody fusion in the treatment of high-degree degenerative disc disease: design of a new device for an "old" technique. A prospective study on a series of 116 patients, Eur Spine J, May 2011: 20 (Suppl 1), pp. 46-56.

Cunningham et al., Design of Interbody Fusion Cages: Historical Considerations and Current Perspectives in Cage Technology; Surgical Techniques, Spinal Implants, pp. 421-465, 2006.

EBI Spine Flyer, North American Spine Society 20th Annual Meeting, Sep. 27-Oct. 1, 2005.

Extended European Search Report for EP 16 15 2952 dated Jul. 1, 2016.

Extended European Search Report including the Written Opinion for Application No. EP 16856190.0 dated May 28, 2019.

Fukuda A, Takemoto M, Tanaka K, Fujibayashi S, Pattanayak DK, Matsushita T, Sasaki K, Nishida N, Kokubo T, Nakamura T. Bone ingrowth into pores of lotus stem-type bioactive titanium implants fabricated using rapid prototyping technique. Bioceramics Development and Applications. Jan. 1, 2011;1, 3 pages.

Kim et al. Spinal Instrumentation Surgical Techniques, Thieme Medical publishers, 2004, pp. 232-245, 518-524, p32-537, 736-743, 795-800.

Kuslich, Lumbar Interbody Cage Fusion for Back Pain: An Update on the Bak (Bagby and Kuslich) System, SPINE: State of the Art Reviews; vol. 13, No. 2, May 1999, pp. 295-311.

Lin et al., Interbody Fusion Gage Design Using Integrated Global Layout and Local Microstructure Topology Optimization; SPINE, vol. 29, No. 16, pp. 1747-1754,2004.

Lin, et al. Structural and mechanical evaluations of a topology optimized titanium interbody fusion cage fabricated by selective laser melting process, Journal of Biomedical Materials Research Part A DOI 10.1 002/jbm.a, pp. 272-279, Apr. 2007.

McAfee, Interbody Fusion Cages in Reconstructive Operations on the Spine, The Journal of Bone and Joint Surgery Incorporated, vol. 81A, No. 6, Jun. 1999, pp. 859-880.

Sasso, Screws, Cages or Both?, <http://www.spineuniverse.com/professional/technology/surgical/thoracic/>, pp. 1-11, Sep. 2012.

Sofamor Danek Interfix Thread Fusion Device, pp. 32-45, 1999.

Stryker, Ttritanium basic science summary, technical monograph, pp. 1-2, 2016.

Synthes Contact Fusion Cage, Technique Guide, 2007, pp. 1-16.

Williams et al., CT Evaluation of Lumbar Interbody Fusion: Current Concepts, AJNR Am J Neuroradiol 26:2057-2066, Sep. 2005.

Zdeblick, et al., L T-CAGE Lumbar Tapered Fusion Device Surgical Technique, Medtronic, pp. 1-25, 2000.

* cited by examiner

SPINAL IMPLANT

CROSS-REFERENCE TO RELATED APPLICATIONS

This application is a continuation of U.S. application Ser. No. 15/007,678, filed on Jan. 27, 2016, which claims priority to U.S. Provisional Patent Application Ser. No. 62/108,197, filed on Jan. 27, 2015, and U.S. Provisional Application No. 62/196,371, filed on Jul. 24, 2015, the entire contents of each of which are hereby incorporated by reference.

BACKGROUND

1. Technical Field

The present disclosure relates to orthopedic surgical devices, and more particularly, to a spinal implant and a method of use.

2. Discussion of Related Art

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions may experience extreme or debilitating pain and diminished nerve function. These conditions and their treatments can be further complicated if the patient is suffering from osteoporosis, or bone tissue thinning and loss of bone density.

Spinal discs between the endplates of adjacent vertebrae in a spinal column of the human body provide critical support. However, due to injury, degradation, disease or the like, these discs can rupture, degenerate, and/or protrude to such a degree that the intervertebral space between adjacent vertebrae collapses as the disc loses at least a part of its support function. This can cause impingement of the nerve roots and severe pain.

In some cases, surgical correction may be required. Some surgical corrections include the removal of the natural spinal disc from between the adjacent vertebrae. In order to preserve the intervertebral disc space for proper spinal column function, an interbody spacer can be inserted between the adjacent vertebrae.

Typically, a prosthetic implant is inserted between the adjacent vertebrae and may include pathways that permit bone growth between the adjacent vertebrae until they are fused together. However, there exists a possibility that conventional prosthetic implants may not provide a fusion due to various conditions and factors, including the fact that the implant does not allow optimal space for bone ingrowth and the implant does not mimic bone density sufficiently to allow for the creation of bone growth factors. In these cases the body rejects the implant and a non-union (no fusion) occurs. When there is a non-union, the implants may be dislodged or moved from their desired implanted location due to movement by the patient or insufficient bone ingrowth.

Therefore, a need exists for a spinal implant that can mimic the density of bone and allow for optimal bone ingrowth and provide a solid fusion of the vertebral segments. In addition, it is desired that an implant be utilized to prevent expulsion of the interbody device by utilizing a spinal plate.

SUMMARY

According to an embodiment of the present disclosure, a spinal implant includes a body portion defining a longitudinal axis, the body portion including a distal end portion, a proximal end portion, opposed side surfaces that extend between the distal and proximal end portions, and top and bottom surfaces configured and adapted to engage vertebral bodies. The top and bottom surfaces have a surface roughness between about 3-4 μm. The spinal implant includes a cavity extending through the top and bottom surfaces defining a surface area that is at least 25% of a surface area of the top surface or the bottom surface. The spinal implant includes first orifices defined through the top surface and second orifices defined through the bottom surface. The second orifices are connected to the first orifices by a plurality of channels.

In embodiments, one of the first orifices may be offset from one of the second orifices.

In embodiments, the spinal implant may have a first plurality of enlarged orifices is defined through one of the top or bottom surfaces and may have a second plurality of enlarged orifices is defined through the other of the top or bottom surfaces. An enlarged orifice of the second plurality of enlarged orifices may include a diameter that is different than a diameter of an enlarged orifice of the first plurality of enlarged orifices. The enlarged orifice of the first plurality of enlarged orifices or the enlarged orifice of the second plurality of enlarged orifices may include a circular cross-section.

In embodiments, the enlarged orifice of the first plurality of enlarged orifices may include a diamond-shaped cross-section and the enlarged orifice of the second plurality of enlarged orifices may include a diamond-shaped cross-section. Each enlarged orifice of the first and second pluralities of enlarged orifices may include a diamond-shaped cross-section.

In embodiments, the spinal implant may have third orifices that are defined through at least one of the opposed side surfaces. One of the third orifices may include a cross-section different than one of the first orifices or one of the second orifices. Opposed openings of one of the third orifices may be offset with respect to each other. One of the third orifices may include a diamond-shaped cross-section.

In embodiments, the spinal implant may have a third plurality of enlarged orifices defined through one of the opposed side surfaces. One enlarged orifice of the third plurality of enlarged orifices may include a diamond-shaped cross-section.

In embodiments, the spinal implant may be formed using an additive manufacturing process.

In embodiments, the spinal implant may have a through-bore defined through the spinal implant. An interior dimension of the through-bore may increase in a direction towards each respective opposed side surface. A bevel may be interposed between each opposed side surface and an interior wall defining the through-bore.

In embodiments, the spinal implant is formed from titanium.

In embodiments, one of the first orifices has a cross-sectional configuration different from that of one of the second orifices.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As commonly known, the term "clinician" refers to a doctor, a nurse, or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is known to indicate a direction toward a patient's head, whereas the term "caudal" indicates a direction toward the patient's feet. Further still, the term "lateral" is understood to indicate a direction toward a side of the body of the patient, i.e., away from the middle of the body of the patient. The term "posterior" indicates a direction toward the patient's back, and the term "anterior" indicates a direction toward the patient's front. Additionally, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring now to FIGS. 1-4, a spinal implant 10 is provided in accordance with the present disclosure and includes a body 12 having a top surface 20, a bottom surface 30, side surfaces 40, a front surface 50, and a rear surface 60. The edges between each of the surfaces of the body 12 may include a bevel or a radius that provide a smooth transition between the adjacent surfaces of the body 12. The top and bottom surfaces 20, 30 are substantially parallel to one another and each includes engagement features 22, 32, respectively, that are configured to permit the spinal implant 10 to move in one direction, e.g., in a direction towards the front surface 20, and prevent or resist movement of the spinal implant 10 in the opposite direction, e.g., in a direction towards the rear surface 60. It is contemplated that the top and bottom surfaces 20, 30 may be disposed at an angle or curved relative to one another, e.g., in a lordotic or a kyphotic relationship to each other, such that the spinal implant 10 is substantially wedge shaped. As shown, the engagement features 22, 32 are rear facing teeth that are configured to engage endplates of adjacent vertebral bodies. The rear surface 60 defines a substantially circular engagement opening 62 that is engagable by a surgical instrument (not shown) to insert and/or reposition the surgical implant 10 between adjacent vertebral bodies.

The top surface 20, the bottom surface 30, and side surfaces 40 have a surface roughness that can promote bone growth and fusion with the spinal implant 10. The surface roughness may be in a range of about 0.10-50 μm, e.g., in a range of about 3-4 μm. In addition, the top surface 20, bottom surface 30, and side surfaces 40 define orifices 24, 34, and 44, respectively, which are sized to promote bone growth into the spinal implant 10. The orifices 24, 34, and 44 are typically circular to mimic bone growth along Haversian canals and lamellar structures of bone. The orifices 24, 34, and 44 may pass entirely through the body 12 of the spinal implant 10 extending orthogonal to the respective surface of the spinal implant 10. Each of the orifices 24 that pass through the top surface 20 may be aligned with a respective one of the orifices 34 that pass through the bottom surface 30. Each of the orifices 24 and 34 are offset from each of the orifices 44. The orifices 24, 34, and 44, have a diameter in the range of about 50-1000 μm, e.g., about 300-700 μm. The orifices 24, 34, and 44 may have varying sizes and shapes between the different surfaces 20, 30, 40 of the spinal implant 10. It is contemplated that the orifices 24, 34, and 44 may vary in size and shape on the same surface 20, 30, 40 of the spinal implant 10. For example, the orifices 24 and 34 are substantially circular in cross-section and the orifices 44 are substantially square in cross-section. The orifices 24, 34, 44 may reduce the density and stiffness of the spinal implant 10 and allow space for applying bone putty or the like to the spinal implant 10 to promote bone growth and fusion of the adjacent vertebral bodies to the spinal implant 10.

Figure 1:
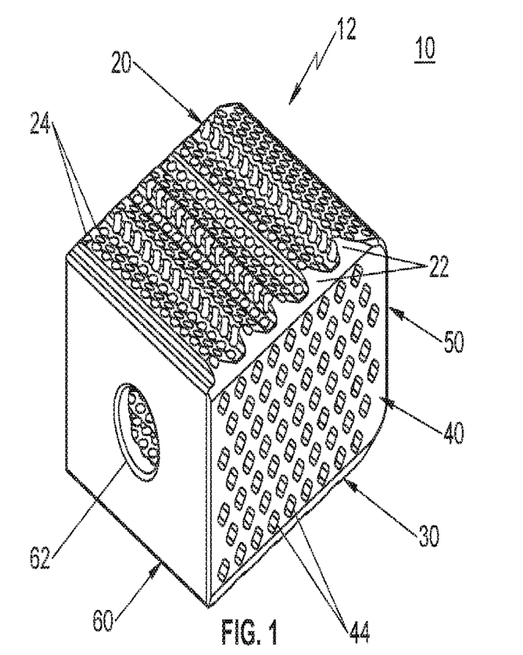
FIG. 1 is a perspective view of an embodiment of a spinal implant provided in accordance with the present disclosure.
Figure 2:
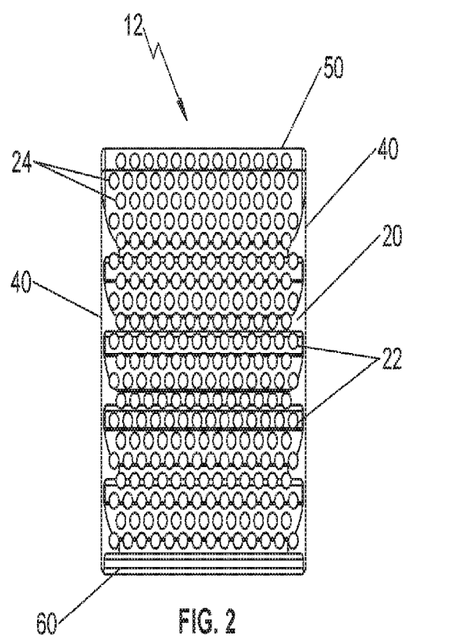
FIG. 2 is a top view of the spinal implant of FIG. 1.
Figure 3:
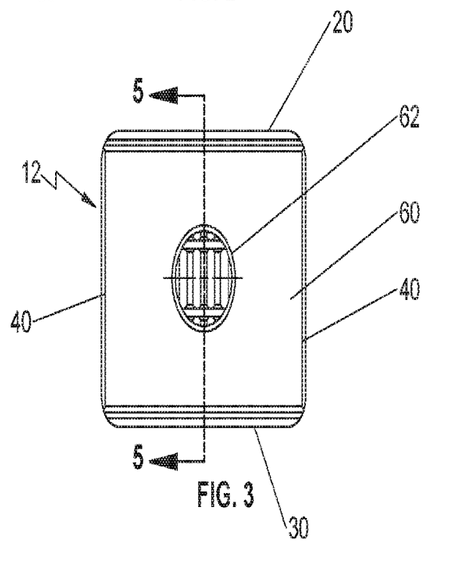
FIG. 3 is a rear view of the spinal implant of FIG. 1.
Figure 4:
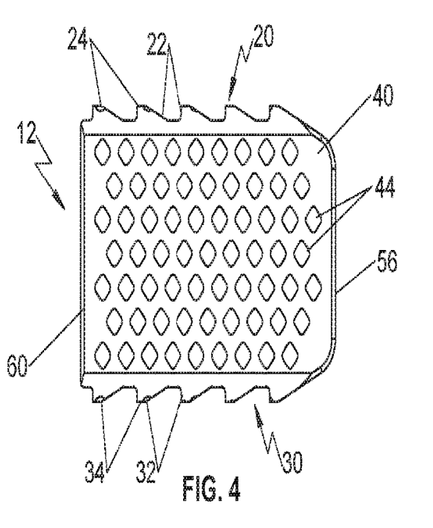
FIG. 4 is a side view of the spinal implant of FIG. 1.

In addition, the spinal implant 10 may define connecting features (not explicitly shown) that further reduce the stiffness of the spinal implant 10. Further, the connecting features may reduce the scatter of the spinal implant 10 during a MRI or CT scan (e.g., when the spinal implant 10 is constructed from titanium). The connecting features also increase the interconnectedness of bone growth through and around the spinal implant 10 which may improve fusion to keep the spinal implant 10 in place and may reduce the chance of breakage of the spinal implant 10. The connecting features may be defined with a width or diameter in a range of about 150-450 μm, e.g., in a range of about 150-380 μm.

Figure 5A:
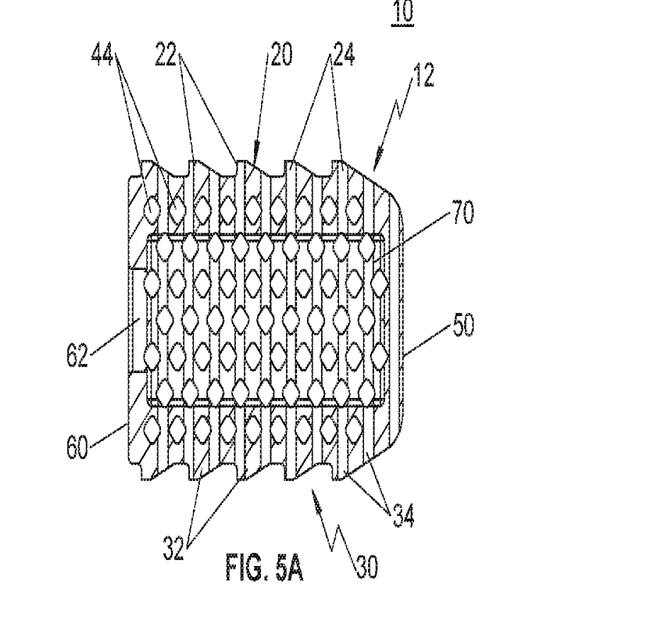
FIG. 5A is a cross-sectional view taken along the section line 5-5 of FIG. 3.
Figure 5B:
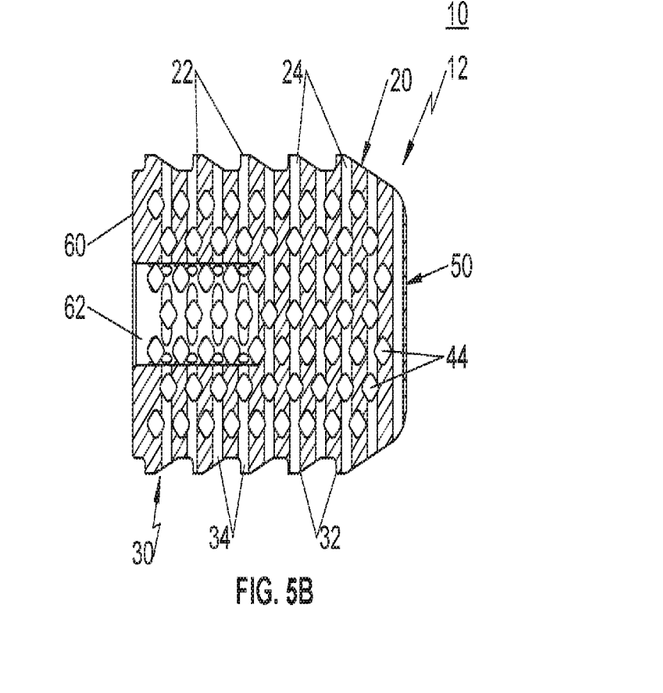
FIG. 5B is a cross-sectional view of a different embodiment of a spinal implant similar to the spinal implant of FIG. 3 taken along the section line 5-5 of FIG. 3.
Figure 6:
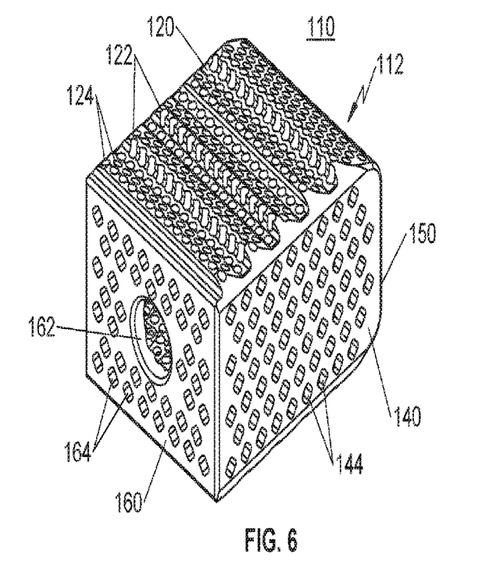
FIG. 6 is a perspective view of another embodiment of a spinal implant provided in accordance with the present disclosure.
Figure 7:
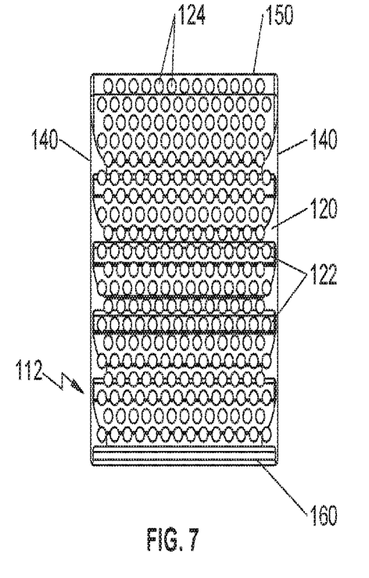
FIG. 7 is a top view of the spinal implant of FIG. 6.
Figure 8:
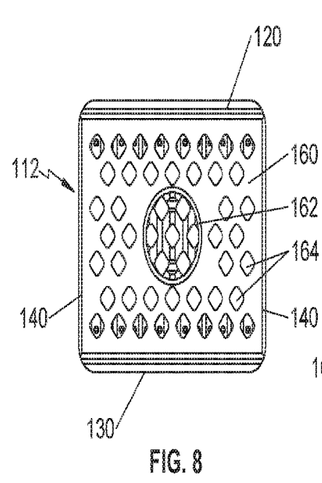
FIG. 8 is a rear view of the spinal implant of FIG. 6.
Figure 9:
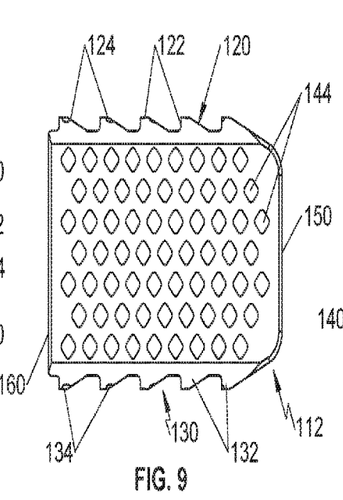
FIG. 9 is a side view of the spinal implant of FIG. 6.
Figure 10:
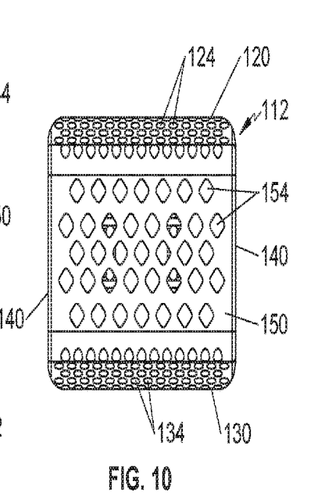
FIG. 10 is a front view of the spinal implant of FIG. 6.
Figure 11:
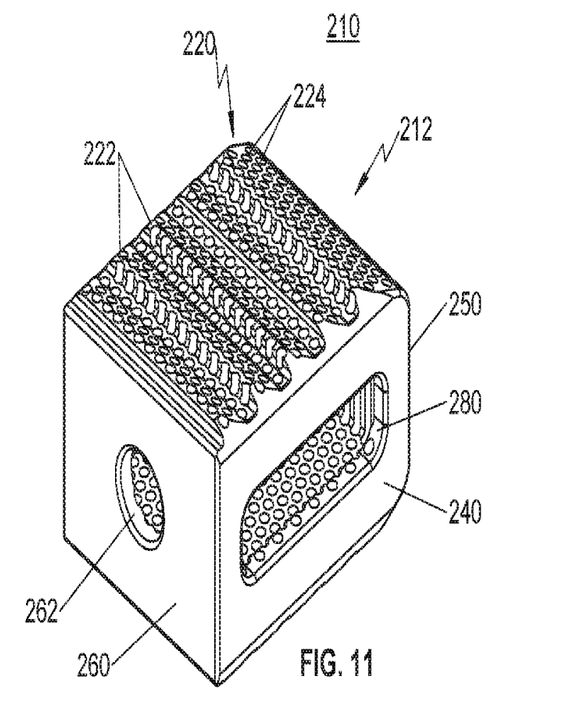
FIG. 11 is a perspective view of another embodiment of a spinal implant provided in accordance with the present disclosure.
Figure 12:
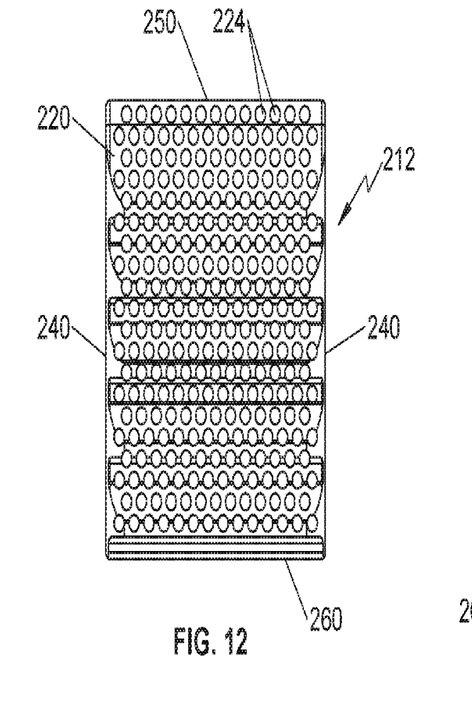
FIG. 12 is a top view of the spinal implant of FIG. 11.
Figure 13:
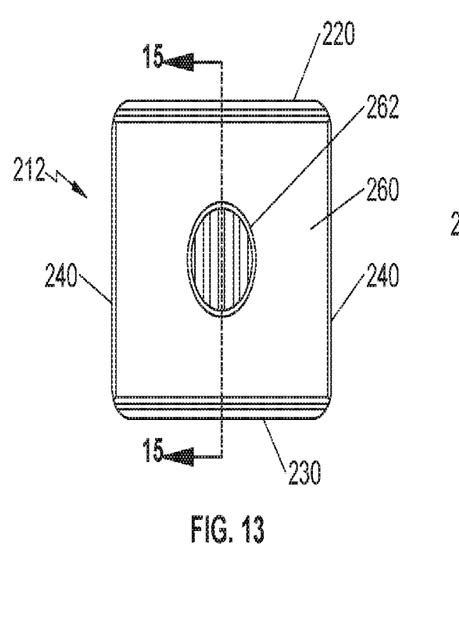
FIG. 13 is a rear view of the spinal implant of FIG. 11.
Figure 14:
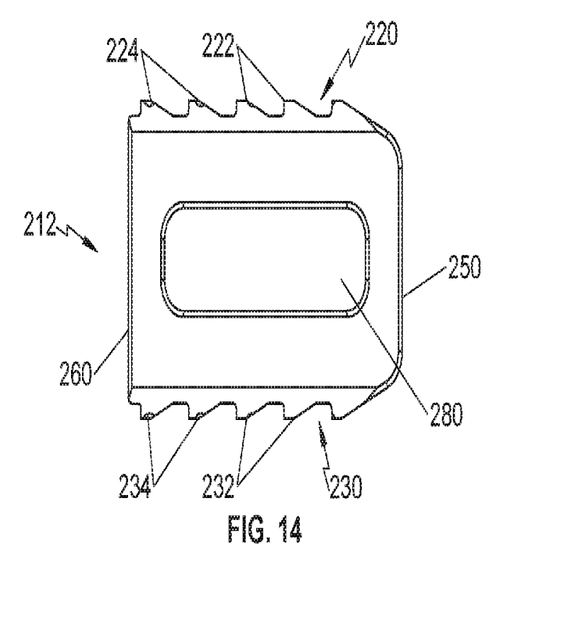
FIG. 14 is a side view of the spinal implant of FIG. 11.

With additional reference to FIG. 5A, the body 12 is hollow and defines an internal cavity 70. As shown in FIG. 5A, each of the top surface 20, the bottom surface 30, side surfaces 40 (FIG. 3), the front surface 50, and the rear surface 60 are thin-walled to define the cavity 70 therebetween. Each of the top surface 20, the bottom surface 30, side surfaces 40 (FIG. 3), the front surface 50, and the rear surface 60 may have a thickness in a range of about 0.009 inches to about 0.020 inches. Alternatively, as shown in FIG. 5B, the body 12 may be substantially solid such that the engagement opening 62 extends into the body 12 towards the front surface 50. In such an embodiment, the engagement opening 62 is a blind hole and may extend in a range of about one quarter to one half of the length of the body 12.

Referring now to FIGS. 6-10, another spinal implant 110 is provided in accordance with the present disclosure. The spinal implant 110 is similar to the spinal implant 10 detailed above with similar structures represented with reference numerals including a "1" preceding the previous reference numeral. Similar features will not be discussed in detail for reasons of brevity. The spinal implant 110 includes a body 112 having a top surface 120, a bottom surface 130, side surfaces 140, a front surface 150, and a rear surface 160. The top surface 120, bottom surface 130, side surfaces 140, the front surface 150, and the rear surface 160 define orifices 124, 134, 144, 154, and 164, respectively, which are sized to promote bone growth into the spinal implant 110. Each of the orifices 154 that pass through the front surface 150 are aligned with a respective one of the orifices 164 that pass through the rear surface 160. In addition, each of the orifices 154, 164 are offset from each of the orifices 124, 134 and each of the orifices 144.

Referring now to FIGS. 11-14, another spinal implant 210 is provided in accordance with the present disclosure. The spinal implant 210 is similar to the spinal implant 10 detailed above with similar structures represented with reference numerals including a "2" preceding the previous reference numeral. Similar features will not be discussed in detail for reasons of brevity.

The spinal implant 210 includes a body 212 having a top surface 220, a bottom surface 230, side surfaces 240, a front surface 250, and a rear surface 260. The top surface 220 and the bottom surface 230 define orifices 224 and 234, respectively. The body 212 defines a lateral window 280 that passes through the side surfaces 240. The lateral window 280 is sized to promote bone growth and fusion with the spinal implant 210. The lateral window 280 may also reduce the density and stiffness of the body 212 of the spinal implant 210. The lateral window 280 may be vertically aligned with the engagement opening 262 of the rear surface 260.

Figure 15A:
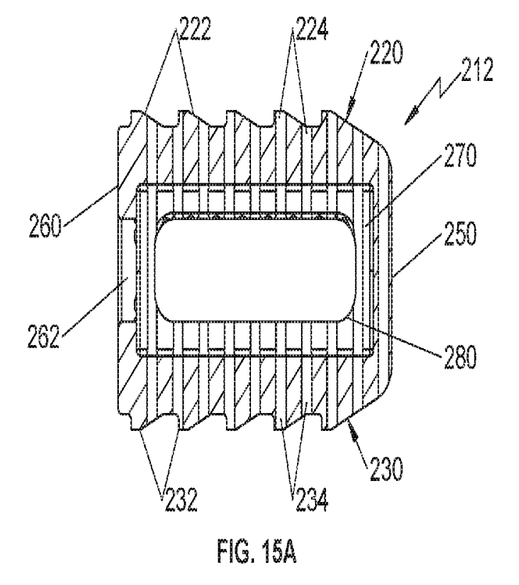
FIG. 15A is a cross-sectional view taken along the section line 15-15 of FIG. 13.
Figure 15B:
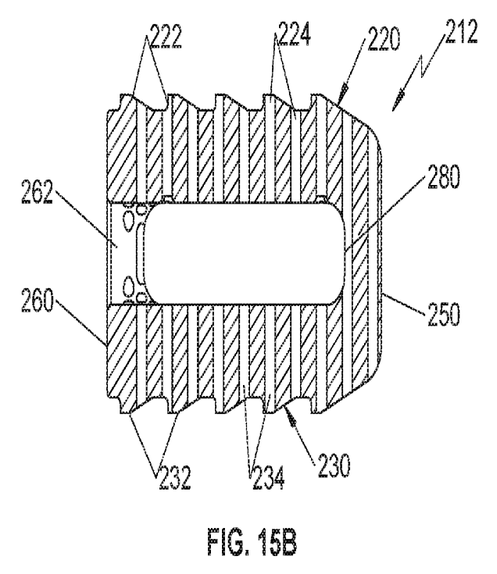
FIG. 15B is a cross-sectional view of a different embodiment of a spinal implant similar to the spinal implant of FIG. 13 taken along the section line 15-15 of FIG. 13.
Figure 16:
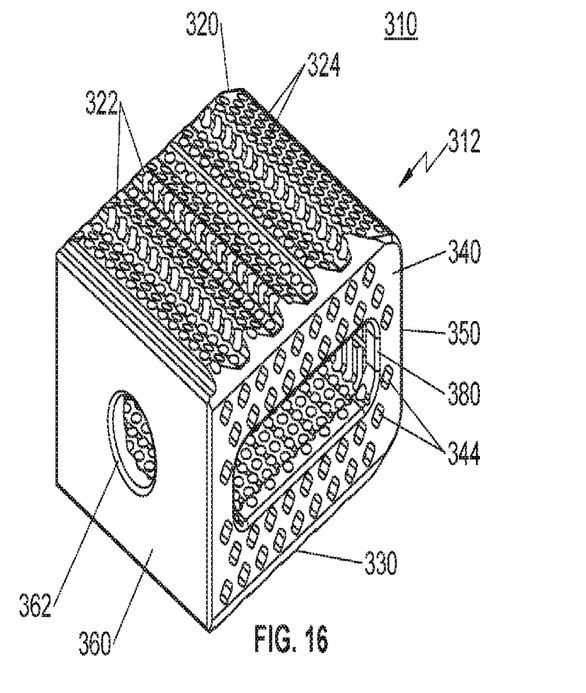
FIG. 16 is a perspective view of another embodiment of a spinal implant provided in accordance with the present disclosure.
Figure 17:
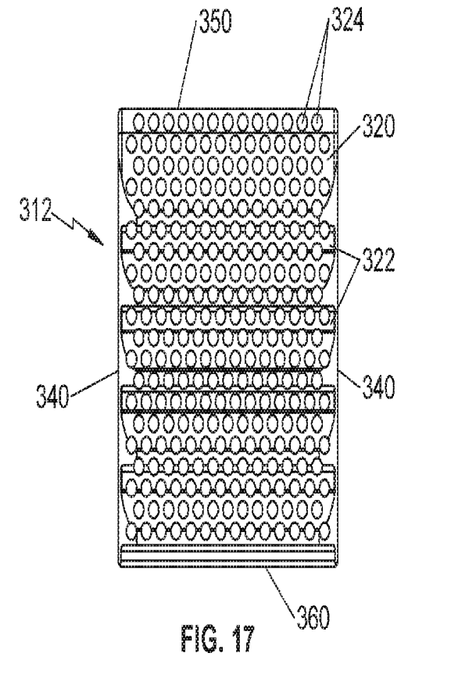
FIG. 17 is a top view of the spinal implant of FIG. 16.
Figure 18:
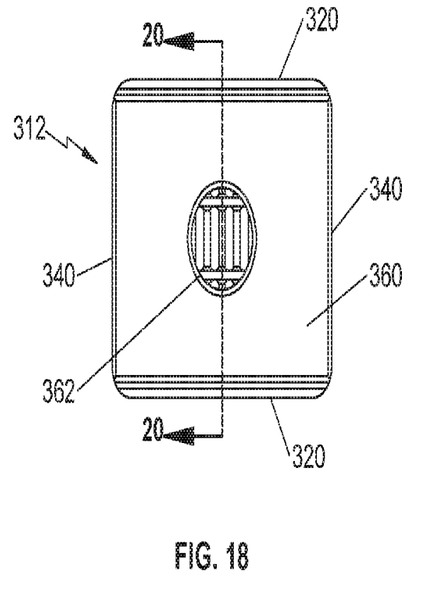
FIG. 18 is a rear view of the spinal implant of FIG. 16.
Figure 19:
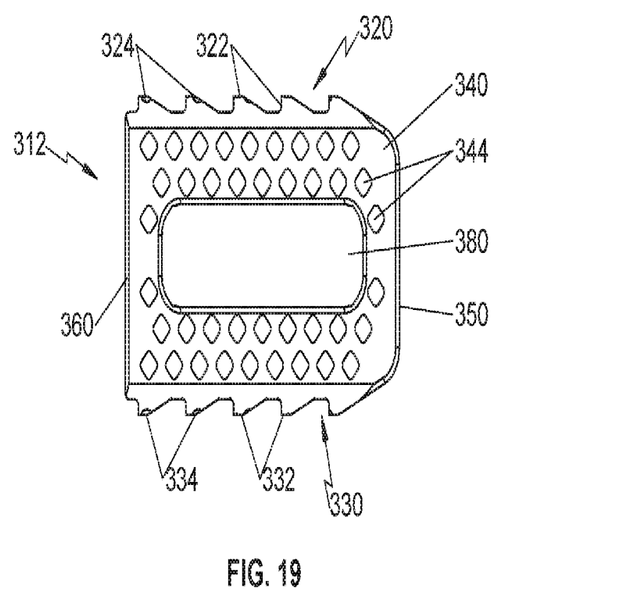
FIG. 19 is a side view of the spinal implant of FIG. 16.

With additional reference to FIG. 15A, the body 212 is hollow and defines an internal cavity 270. As shown in FIG. 15A, each of the top surface 220, the bottom surface 230, side surfaces 240 (FIG. 11), the front surface 250, and the rear surface 260 are thin-walled to define the cavity 270 therebetween. Alternatively, as shown in FIG. 15B, the body 212 may be substantially solid such that the engagement opening 262 extends into the body 212 towards the front surface 250. In such an embodiment, the diameter of the engagement opening 262 may be substantially equal to a height of the lateral window 280.

Referring now to FIGS. 16-19, another spinal implant 310 is provided in accordance with the present disclosure. The spinal implant 310 is similar to the spinal implant 10 detailed above with similar structures represented with reference numerals including a "3" preceding the previous reference numeral. Similar features will not be discussed in detail for reasons of brevity.

The spinal implant 310 includes a body 312 having a top surface 320, a bottom surface 330, side surfaces 340, a front surface 350, and a rear surface 360. The top surface 320, side surfaces 340, and the bottom surface 330 define orifices 324, 334, and 344, respectively. The spinal implant 310 defines a lateral window 380 that passes through the side surfaces 340 which is similar to the lateral window 280 of the body 212 of the spinal implant 210 detailed above.

Figure 20A:
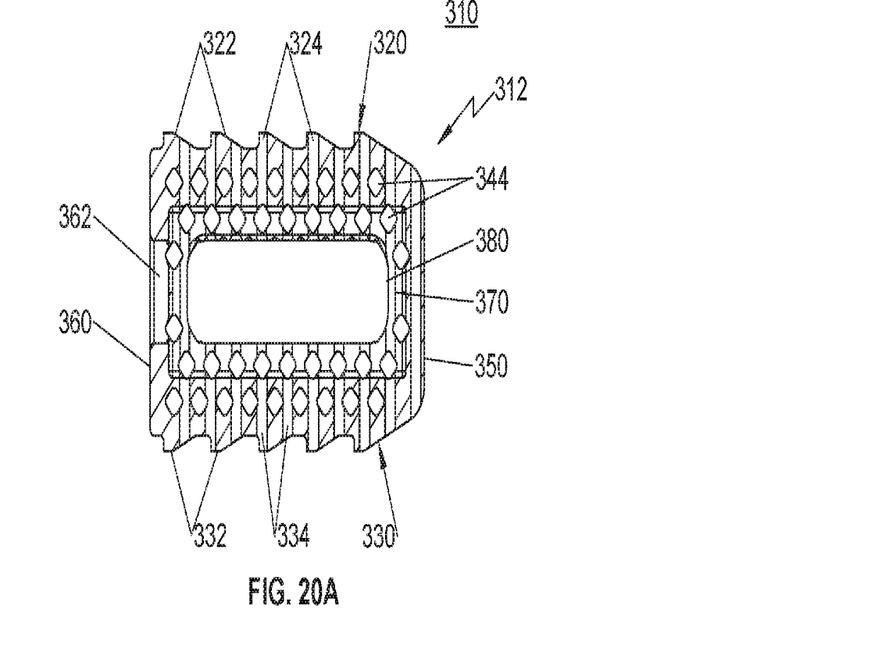
FIG. 20A is a cross-sectional view taken along the section line 20-20 of FIG. 18.
Figure 20B:
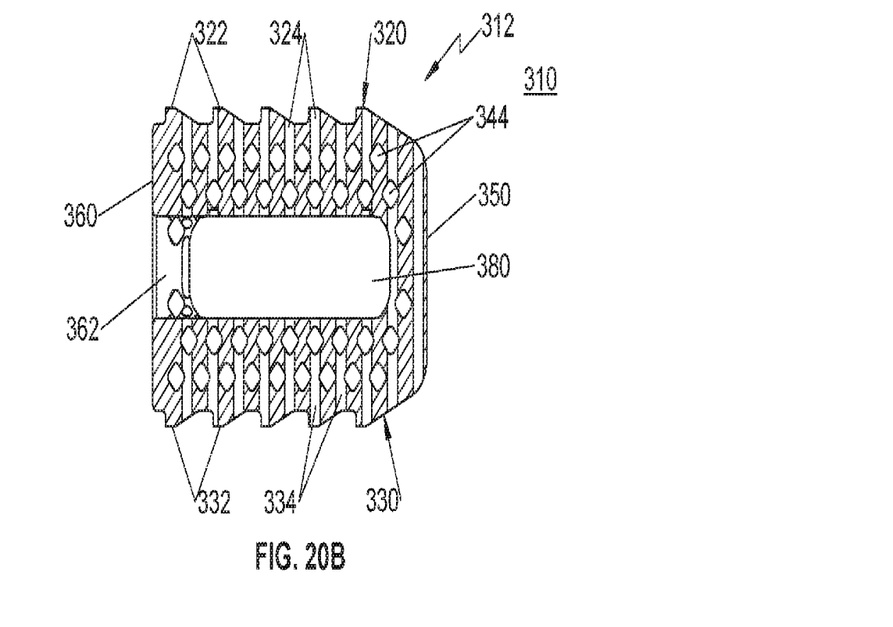
FIG. 20B is a cross-sectional view of a different embodiment of a spinal implant similar to the spinal implant of FIG. 18 taken along the section line 20-20 of FIG. 18.

With additional reference to FIG. 20A, the body 312 is hollow and defines an internal cavity 370. As shown in FIG. 20A, each of the top surface 320, the bottom surface 330, side surfaces 340 (FIG. 16), the front surface 350, and the rear surface 360 are thin-walled to define the cavity 370 therebetween. Alternatively, as shown in FIG. 20B, the body 312 may be substantially solid such that the engagement opening 362 extends into the body 312 towards the front surface 350. In such an embodiment, the diameter of the engagement opening 362 may be substantially equal to a height of the lateral window 380.

Figure 21:
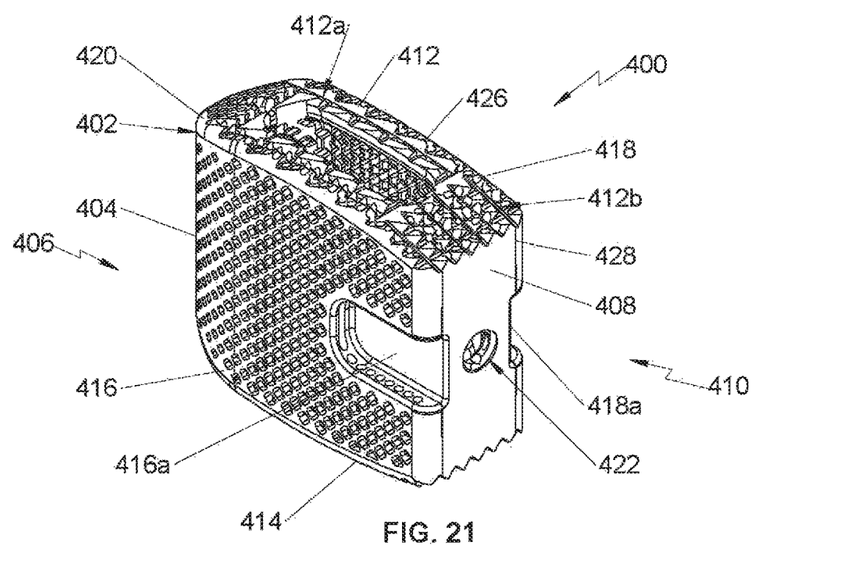
FIG. 21 is a perspective view of yet another embodiment of a spinal implant provided in accordance with the present disclosure.
Figure 22:
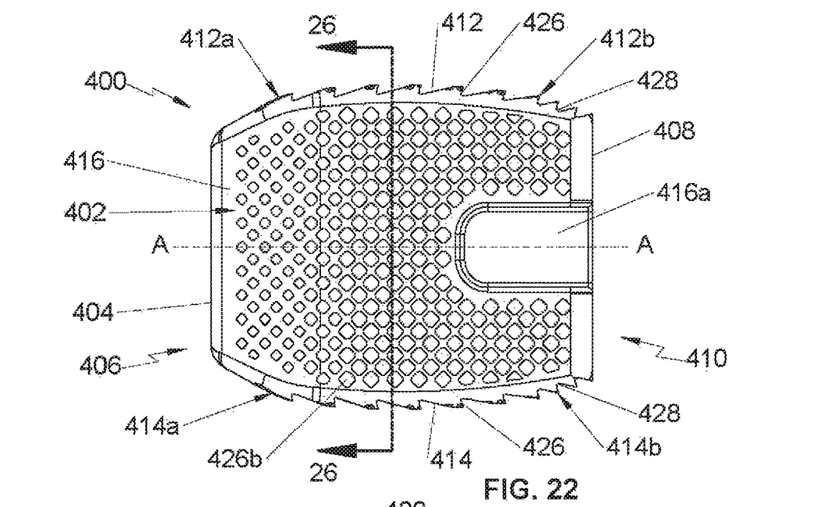
FIG. 22 is a side view of the spinal implant of FIG. 21.
Figure 23:
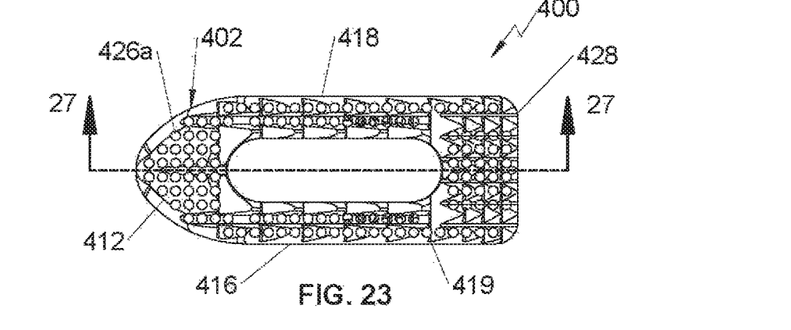
FIG. 23 is a top view of the spinal implant of FIG. 21.

Referring to FIGS. 21-23, yet another embodiment of a spinal implant provided in accordance with the present disclosure is illustrated and generally identified by reference numeral 400. Spinal implant 400 includes a body 402 having a substantially contoured first end surface 404 at a distal or leading end 406 and a second end surface 408 opposite thereto at a proximal or trailing end 410, having a substantially planar configuration. Axis A-A is defined through a midpoint of first and second end surfaces 404, 408, respectively. Body portion 402 extends between first and second end surfaces 404, 408 to define respective top and bottom surfaces 412 and 414 (FIG. 22), respectively, as well as opposed side surfaces 416, 418 (FIG. 23). As best illustrated in FIG. 22, top and bottom surfaces 412, 414 include a generally convex or arcuate profile, each extending in a cephalad and caudal direction, respectively. Although shown and discussed as the top surface 412 being oriented in a cephalad direction and the bottom surface 414 being oriented in a caudal direction, the implant 400 may be positioned such that the top surface 412 in a caudal orientation and the bottom surface 414 is in a cephalad orientation. As can be appreciated, top and bottom surfaces 412, 414 may include a concave profile, a planar profile, or any combination thereof. In embodiments, top surface 412 may include a different profile than that of bottom surface 414. Additionally, it is contemplated that top and bottom surfaces 412, 414 may approximate towards each other in a distal direction along axis A-A (or vice versa), or may approximate towards each other in a direction from side surface 416 towards side surface 418 (or vice versa), or any combination thereof.

As best illustrated in FIG. 23, opposed side surfaces 416, 418 are substantially planar, although other configurations are also contemplated such as convex, concave, or the like. Opposed side surfaces 416, 418 approximate towards each other at distal end 406 along longitudinal axis A-A in order to facilitate insertion within the intervertebral space and enhance the atraumatic character of body portion 402. In this manner, the intersection of top and bottom surfaces 412, 414 with each of first and second end surfaces 404, 408 and opposed side surfaces 416, 418 may include a fillet or rounded configuration 420 to inhibit sharp edges from causing trauma to the surrounding tissue and/or vertebral bodies.

Referring again to FIG. 21, second end surface 408 includes an aperture 422 defined therethrough and extending along longitudinal axis A-A. Aperture 422 is configured for selective engagement with a suitable insertion tool (not shown), such as that described in U.S. Patent Application Serial No. 2012/0158062, filed Oct. 11, 2011, the entire contents of which are hereby incorporated by reference herein. In embodiments, aperture 422 may be threaded or otherwise include various features capable of selectively retaining a suitable insertion tool therein, such as a keyhole configuration, quarter turn configuration, or the like.

Each of opposed side surfaces 416, 418 include a corresponding depression or recess 416a, 418a defined therein adjacent second end surface 408. Recesses 416a, 418a extend along longitudinal axis A-A and are symmetrically disposed on each of opposed side surfaces 416, 418 to define a substantially I-shaped configuration to second end surface 408 at proximal end 410. In cooperation with aperture 422, the recesses 416a, 418a are further configured to enable engagement with stabilizing jaws of a suitable insertion instrument to facilitate the insertion of spinal implant 400.

Body 402 includes a through-bore or cavity 424 defined through top and bottom surfaces 412, 414, respectively. Although shown as having a generally oval configuration, it is contemplated that through-bore 424 may include any suitable shape, such as square, rectangular, circular, or the like, or may include a configuration similar to that of the outer perimeter of body 402. It is contemplated that through-bore 424 may receive allograft material, autograft material, calcium phosphate/bone marrow aspirate (BMA), autogenous material, synthetic materials comprised of a biocompatible, osteoconductive, osteoinductive, or osteogeneic material such as VITOSS® Synthetic Cancellous Bone Void Filler material, or any other suitable biological material known in the art. Through-bore 424 includes a cross-sectional area or surface area that is greater than any orifice of the plurality of orifices or enlarged orifices detailed hereinbelow. In embodiments, through-bore 424 includes a surface area that is equal to or greater than 25% of the surface area of top surface 412 or bottom surface 414.

Top and bottom surfaces 412, 414 of body portion 402 are configured to engage respective endplates of adjacent vertebral bodies. In this manner, each of top and bottom surfaces 412, 414 include at least first and second surface regions 412a, 412b and 414a, 414b, respectively, which have distinct surface characteristics. As best illustrated in FIG. 22, first surface regions 412a, 414a are disposed distal to second surface regions 412b, 414b and include a surface characteristic that is different than that of second surfaces 412b, 414b. In embodiments, first surface regions 412a, 414a may include a same or similar surface characteristic to that of second surface regions 412b, 414b, or each of first and second surface regions 412a, 414a and 412b, 414b may include the same or different surface characteristics, or any combination thereof.

First surface regions 412a, 414a have a plurality of protrusions (i.e., teeth) or ridges 426 disposed thereon to aid in securing spinal implant 400 to each respective adjacent vertebral body and stability against fore and aft, oblique or side to side movement of spinal implant 400 within the intervertebral space. Specifically, ridges 426 frictionally engage endplates of adjacent vertebral bodies and inhibit movement of the spinal implant 400 with respect to the adjacent vertebral bodies. In embodiments, a longitudinal groove 419 (FIG. 23) may be defined between adjacent rows of protrusions 426, each of which extends along axis A-A. Each of second surface regions 412b, 414b includes substantially pyramidal protrusions 428, where each pyramidal protrusion 428 includes a plurality of protrusions or ridges disposed thereon to similarly aid in securing spinal implant 400 to each respective adjacent vertebral body. In particular, each pyramidal protrusion 428 includes opposed first and second faces that face, respectively, distally and proximally. Further, each pyramidal protrusion 428 has third and fourth faces that face, respectively, medially and laterally. For a detailed description of spinal implant having exemplary surface characteristics, reference can be made to U.S. Pat. No. 8,801,791 to Soo et al., the entire contents of which are hereby incorporated by reference herein.

Spinal implant 400 is constructed of a biocompatible material, such as commercially pure titanium or titanium alloy and includes a porosity capable of promoting bone ingrowth and fusion with spinal implant 400. In this manner, top and bottom surfaces 412, 414 and opposed side surfaces 416, 418 have a surface roughness that can promote bone growth and fusion with spinal implant 400. The surface roughness may be in a range of about 0.10-50 μm, and preferably in a range of about 3-4 μm. As can be appreciated, top and bottom surfaces 412, 414 and opposed side surfaces 416, 418 may include the same or different surface roughness's (i.e., the surface roughness of top surface 416 may be different than the surface roughness of bottom surface 414), or top and bottom surfaces 412, 414 and opposed side surfaces 416, 418 may not include a surface roughness;

rather, top and bottom surfaces 412, 414 and opposed side surfaces 416, 418 may be smooth. In embodiments top and bottom surfaces 412, 414 and opposed side surfaces 416, 418 may include any combination of surface roughness or smooth surface. Additionally, body 402 includes a plurality of orifices 426a and 426b defined through top and bottom surfaces 412, 414 and opposed side surfaces 416, 418, respectively, configured to promote bone ingrowth. Orifices 426a, 426b include a generally circular and diamond shaped cross-section, respectively, although other suitable cross-sections capable of promoting bone ingrowth are contemplated, such as oval, square, hexagonal, rectangular, or the like. The circular and diamond shaped-cross sections of orifices 426a, 426b, respectively, mimic bone growth along Haversian canals and lamellar structures of bone. In this manner, orifices 426a, 426b may pass entirely through top surface and bottom surfaces 412, 414 and opposed surfaces 416, 418, respectively. Alternatively, orifices 426a may be offset in relation to one another, and similarly with orifices 426b. In the interest of brevity, only orifices 426a will be described in detail herein below with respect to the offset nature of orifices 426a and 426b. An orifice 426a defined through bottom surface 414 will be offset from a corresponding orifice 426a defined through top surface 412. In embodiments, orifices 426a may be defined through top and bottom surfaces 412, 414 normal thereto or at angles relative thereto. In one non-limiting embodiment, orifices 426a are defined through top and bottom surfaces 412, 414 at angles incident relative to each other, thereby forming a chevron configuration. As can be appreciated, each of the orifices 426a and 426b formed through top and bottom surfaces 412, 414 and opposed side surfaces 416,418, respectively, form a respective channel therebetween, thereby interconnecting an orifice formed through top surface 416 and an orifice formed through bottom surface 414, or an orifice formed through side surface 416 and an orifice formed through side surface 418. It is contemplated that the density of orifices 426a may be different on top surface 412 than on bottom surface 414, or may increase or decrease in density at various locations on each of top and bottom surfaces 412, 414. Orifices 426a include a diameter in a range of about 50-1000 µm, although a diameter between 300-700 µm is preferable. As can be appreciated, for shapes other than circular, orifices 426a include a cross-sectional area in a range of about 0.0019 µm$^2$-0.785 µm$^2$, although a cross-sectional area between 0.0707 µm$^2$-0.385 µm$^2$ is preferable. As can be appreciated, the plurality of orifices 426a may include orifices 426a having varying sizes and shapes relative to each other. In embodiments, the orifices 426a defined through top surface 412 may include a different cross-section than those orifices 426a defined through bottom surface 414 (i.e., circular on top surface 412 while square on bottom surface 414, or vice versa). The plurality of orifices 426a reduce the density and stiffness of spinal implant 400 to enable the application of bone putty or the like (e.g., Bone Morphogenetic Proteins (BMP), etc.) to spinal implant 400 to promote bone ingrowth within spinal implant 400 and fusion to adjacent vertebral bodies. Bone ingrowth and fusion strengthens spinal implant 400. In this manner, the likelihood that micromotion would occur would likewise be reduced.

Figure 24:
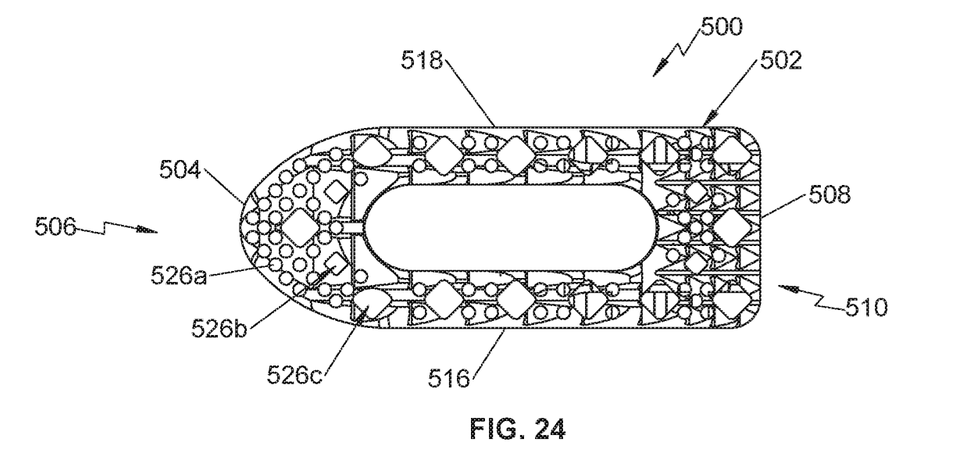
FIG. 24 is a top view of a different embodiment of a spinal implant similar to the spinal implant of FIG. 21.

Referring to FIG. 24, another embodiment of a spinal implant provided in accordance with the present disclosure is illustrated and generally identified by reference numeral 500. Spinal implant 500 is substantially similar to spinal implant 400, and therefore, only the differences therebetween will be described in detail in the interest of brevity. Body 502 includes a first plurality of enlarged orifices 526c defined through top and bottom surfaces 512, 514. The first plurality of enlarged orifices 526c is arranged around the perimeter of body 502. In one non-limiting embodiment, the first plurality of enlarged orifices 526c are disposed approximately equidistant between opposed side surfaces 516, 518, through-bore 524, and first and second end surfaces 504, 508. A second plurality of enlarged orifices 526d is defined through top and bottom surfaces 512, 514 on each of the leading and trailing ends 508, 510, and includes a smaller diameter than that of the first plurality of enlarged orifices 526c. In this manner, the second plurality of enlarged orifices 526d is interposed between the first plurality of enlarged orifices 526c disposed on the leading and trailing ends 508, 510 and through-bore 524. Although illustrated as having a generally diamond shaped cross-section, it is contemplated that the first and second plurality of enlarged orifices 526c, 526d may include any suitable cross-section, such as circular, oval, square, hexagonal, rectangular, or the like. As can be appreciated, the first and second plurality of enlarged orifices 526c, 526d may be defined through top and bottom surfaces 512, 514 in any manner similar as described above with respect to spinal implant 400.

A plurality of orifices 526a is defined through top and bottom surfaces 512, 514, similarly to that described above with respect to spinal implant 400; however, the plurality of orifices 526a is interposed between each of the first and second plurality of enlarged orifices 526c, 526d.

Figure 25:
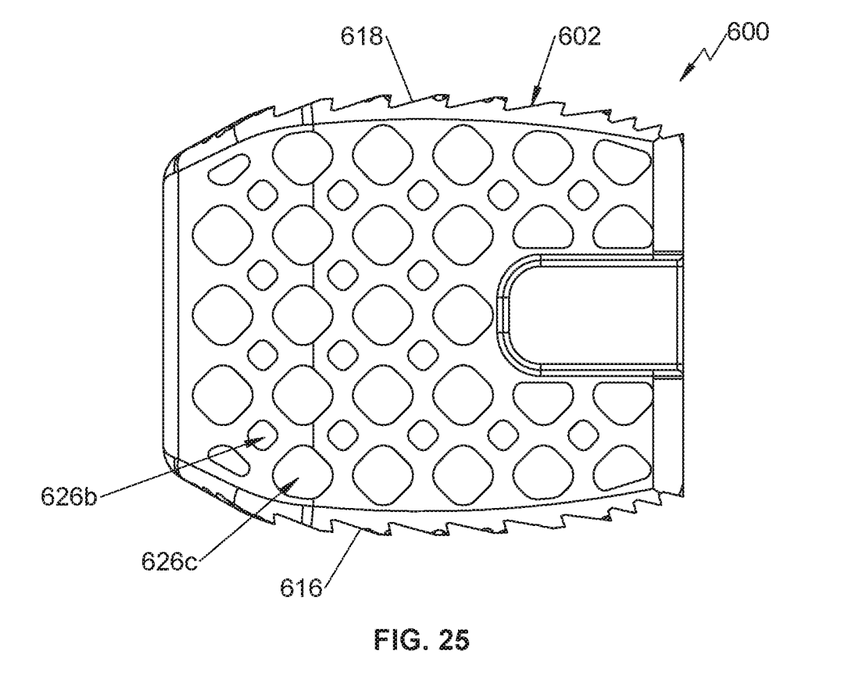
FIG. 25 is a side view of a different embodiment of a spinal implant similar to the spinal implant of FIG. 21.

Turning now to FIG. 25, still another embodiment of a spinal implant provided in accordance with the present disclosure is illustrated and generally identified by reference numeral 600. Spinal implant 600 is substantially similar to spinal implant 400, and therefore, only the differences therebetween will be described in detail in the interest of brevity. Body 602 includes a plurality of enlarged orifices 626c defined through opposed side surfaces 616, 618. In this manner, the plurality of enlarged orifices 626c is interposed between each orifice 626b defined through opposed side surfaces 616, 618 such that the orifices of the plurality of enlarged orifices 626c and orifices 626b are arranged in an alternating pattern. Although illustrated as having a generally diamond shaped cross-section, it is contemplated that the plurality of enlarged orifices 626c may include any suitable cross-section, such as circular, oval, square, hexagonal, rectangular, or the like.

As can be appreciated, the features of spinal implants 500 and 600 may be combined, such that spinal implant 500 may further include the plurality of enlarged orifices 626c defined through opposed side surfaces 516, 518, or spinal implant 600 may include the first and second pluralities of enlarged orifices 526c, 526d defined through top and bottom surfaces 612, 614.

Figure 26:
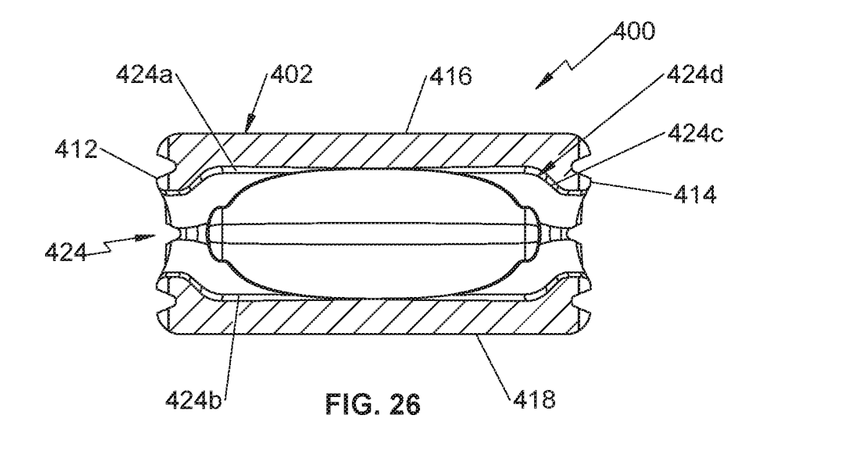
FIG. 26 is a front, cross-sectional view, of the spinal implant of FIG. 21 taken along section line 26-26 of FIG. 22.
Figure 27:
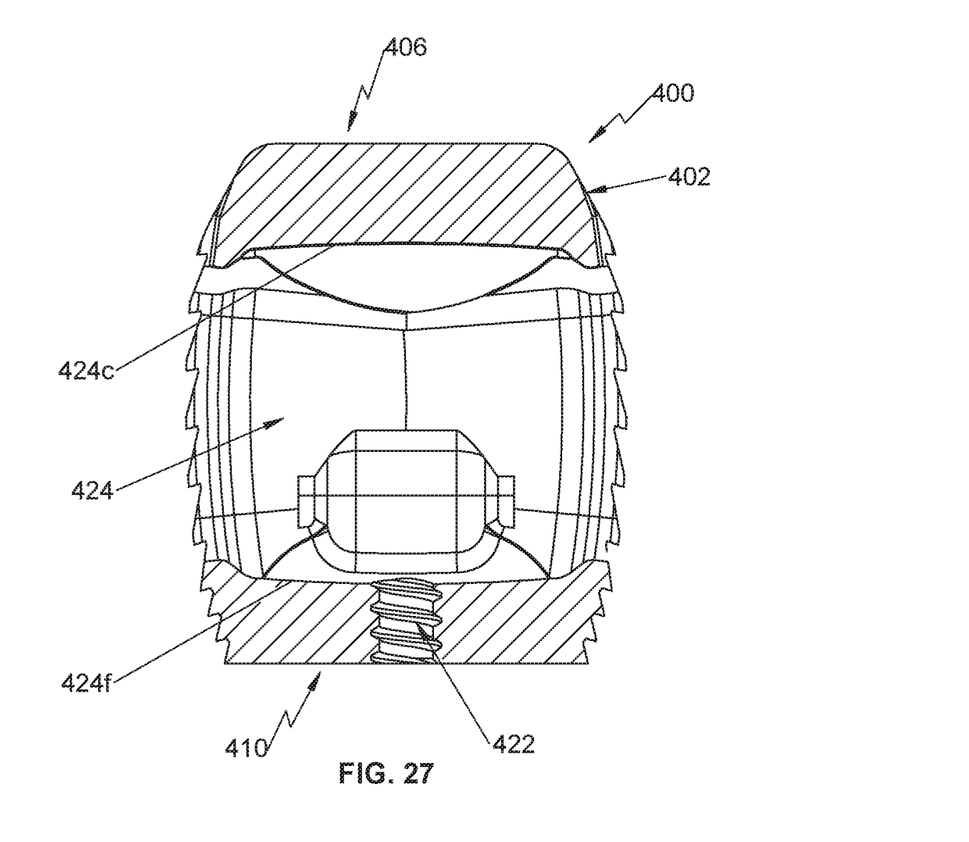
FIG. 27 is a bottom, cross-sectional view, of the spinal implant of FIG. 21, taken along section line 27-27 of FIG. 23.

With reference to FIGS. 26 and 27, front and bottom cross-sectional views of spinal implant 400 are illustrated. The interior dimensions of through-bore 424 increase in a direction towards opposed side walls 416, 418. In this manner, through-bore 424 is configured to receive a greater amount of biological material than is possible with a through-bore having planar side walls. Through-bore 424 includes a pair of opposed interior surfaces 424a and 424b adjacent opposed side surfaces 416, 418. Although generally illustrated as defining a planar configuration, it is contemplated that opposed interior surfaces 424a, 424b may include any suitable configuration, such as convex, concave, may approximate each other in a cephalad or caudal direction, or approximate each other in a distal or proximal direction, or any combination thereof. As best illustrated in FIG. 26, through-bore 424 includes a bevel or undercut 424c extending in an interior direction from each of opposed side surfaces 416, 418 and towards a respective opposed interior surface 424a, 424b. The undercut 424c aids in retaining the bone growth material therein, reducing the possibility that the bone growth material may become separated or dislodged from spinal implant 400. Further still, providing spinal implant 400 with an undercut 424c allows implant 400 to house a larger volume of bone growth material or other biologics as compare to a spinal implant lacking an undercut. Although illustrated as including a fillet 424d joining undercut 424c and opposed interior surfaces 424a, 424b, it is contemplated that the intersection of undercut 424c and a respective opposed interior surface 424a, 424b may include any suitable joining feature, such as a sharp corner, bevel, or the like.

As best illustrated in FIG. 27, through-bore 424 includes generally planar end surfaces 424e and 424f at leading and trailing ends 406, 410, respectively. As can be appreciated, each of planar end surfaces 424e, 424f may include any suitable profile, such as concave, convex, may approximate one another in a cephalad direction, may approximate one another in a caudal direction, may approximate one another in a distal direction, a proximal direction, or any combination thereof.

As can be appreciated, manufacturing spinal implants 10, 110, 210, 310, 400, 500, and 600 using standard machining methods (e.g., lathe, mill, EDM, etc.) would be difficult. In view of this, it is contemplated that spinal implants 10, 110, 210, 310, 400, 500, and 600 may be manufactured by means of additive manufacturing methods (e.g., SDM, SLPP, DMLS (i.e., EOS), SLS, SLM, SHS, EBM, VAT photopolymerisation, material jetting, binder jetting, or the like). As each of spinal implants 10, 110, 210, 310, 400, 500, and 600 may be constructed in a similar fashion, only the method of constructing spinal implant 400 utilizing additive manufacturing methods will be described herein in the interest of brevity. In one non-limiting embodiment, spinal implant 400 may be manufactured using Selective Laser Powder Processing (SLPP). SLPP utilizes powdered metal and a laser which sinters or cures the metal in a selective fashion according to the design intent in thin layers. In embodiments, the layers may have a thickness of about 250 µm. Spinal implant 400 is built layer by layer to allow for more design options and features which would be difficult to be machined using conventional methods. Specifically, a first layer of powder is applied to a specialized build plate, at which point the laser cures portions of the powder according to the design intent. At this point, a second layer is applied to the build plate and the laser is again used to cure selective portions of this second layer. This process is repeated until spinal implant 400 is fully formed. Once spinal implant 400 is fully formed, uncured powder is removed using compressed air or other similar means. Next, post machining is performed on spinal implant 400 to remove any burrs or similar imperfections embedded within spinal implant 400 during the additive manufacturing process. In embodiments, the burrs are removed by means of buffer wheels, clippers, files, or the like. Once de-burred, spinal implant 400 is heat treated, and thereafter, media blasted using aluminum oxide. Thereafter, spinal implant 400 is immersed in a hydrofluoric bath to strip the aluminum oxide therefrom. Finally, spinal implant 400 is inspected by quality control personnel (or using automated means), cleaned via ultrasonic cleaning, dried, and packaged. Additionally, using SLPP, it is contemplated that spinal implant 400 may be customized for a designated patient. For a detailed description of exemplary manufacturing methods, reference can be made to U.S. Pat. No. 8,590,157, issued on Nov. 6, 2013 to Kruth et al., the entire contents of which are hereby incorporated by reference herein.

Each of spinal implants 10, 110, 210, 310, 400, 500, and 600 may be constructed from titanium, a titanium-alloy, a cobalt-chromium alloy, a ceramic, Polyetheretherketone, or any other suitable biocompatible material. It is also contemplated that spinal implants 10, 110, 210, 310, 400, 500, and 600 may be manufactured using a three-dimensional printer utilizing a biocompatible polymer.

It is envisioned that the manufacturing processes and orifice designs detailed above may be utilized to form various other medical devices known in the art. In this manner, the additive manufacturing process detailed above may be employed to form corpectomy devices, fixed spinal implants, expandable spinal implants, bone screws, cervical implants, and the like. Similarly, the orifice designs detailed above may be formed in any of the beforementioned medical devices that would benefit from an increased ability to fuse with bone. Examples of such devices may be found in the following commonly owned references: U.S. Pat. No. 8,585,761 to Theofilos, U.S. Pat. No. 8,673,011 to Theofilos et al., U.S. application Ser. No. 14/936,911 to Sutterlin et al., U.S. Pat. No. 8,801,791 to Soo et al., U.S. Pat. No. 8,439,977 to Kostuik et al., U.S. Patent Application Publication No. 2010/0100131 to Wallenstein, U.S. Patent Application Publication No. 2012/0179261 to Soo, U.S. Pat. No. 8,449,585 to Wallenstein et al., U.S. Pat. No. 8,814,919 to Barrus et al., U.S. Pat. No. 5,733,286 to Errico et al., and U.S. Patent Application Publication No. 2013/0046345 to Jones et al.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

The invention claimed is:

1. A spinal implant comprising:
    a body portion defining a longitudinal axis, the body portion including a distal end portion, a proximal end portion, opposed side surfaces that extend from the distal end portion to the proximal end portion, and top and bottom surfaces configured and adapted to engage vertebral bodies;
    the top and bottom surfaces include engagement features configured to engage vertebral bodies adjacent the spinal implant to permit the spinal implant to move in one direction and prevent the spinal implant from moving in an opposite direction;
    first orifices defined through the top surface, each orifice of the first orifices defining a respective centerline therethrough;
    second orifices defined through the bottom surface each orifice of the second orifices defining a respective centerline therethrough, the second orifices connected to the first orifices by a plurality of first channels, the first channels defining a plurality of first channel rows;
    wherein a first plurality of enlarged orifices is defined through the top and bottom surfaces to form a plurality of second channels, the second channels defining a plurality of second channel rows, each second channel row being interposed between first channel rows.

2. The spinal implant of claim 1, further comprising third orifices defined through at least one of the opposed side surfaces, the third orifices defining respective centerlines therethrough, wherein the centerlines of the third orifices extend through the plurality of first channels.

3. The spinal implant of claim 2, further comprising fourth orifices extending from one opposed side surface to the other opposed side surface, the fourth orifices defining respective centerlines therethrough, wherein the centerlines of the fourth orifices extend between the plurality of first channels.

4. The spinal implant of claim 1, further comprising a cavity extending through the top and bottom surfaces, the cavity defining a surface area that is at least 25% of a surface area of the top surface or the bottom surface.

5. The spinal implant of claim 1, wherein the top and bottom surfaces have a surface roughness between 3-4 µm.

6. The spinal implant of claim 1, wherein the distal end portion includes an engagement opening that is configured to be releasably engaged with a surgical instrument.

7. The spinal implant of claim 6, wherein the body defines a lateral window that passes through each of the side surfaces.

8. The spinal implant of claim 7, wherein the lateral window has a height equal to the diameter of the engagement opening, and wherein the lateral window is vertically aligned with the engagement opening.

9. A spinal implant comprising:
a body portion defining a longitudinal axis, the body portion including a distal end portion, a proximal end portion, opposed side surfaces that extend from the distal end portion to the proximal end portion, and top and bottom surfaces configured and adapted to engage vertebral bodies;
first orifices defined through the top surface, each orifice of the first orifices defining a respective centerline therethrough;
second orifices defined through the bottom surface each orifice of the second orifices defining a respective centerline therethrough, the second orifices connected to the first orifices by a plurality of first channels, the first channels defining a plurality of first channel rows;
third orifices defined through at least one of the opposed side surfaces, the third orifices defining respective centerlines therethrough, wherein the centerlines of the third orifices extend through the plurality of first channels, and
fourth orifices extending from one opposed side surface to the other opposed side surface, the fourth orifices defining respective centerlines therethrough, wherein the centerlines of the fourth orifices extend between the plurality of first channels,
wherein a first plurality of enlarged orifices is defined through the top and bottom surfaces to form a plurality of second channels, the second channels defining a plurality of second channel rows, each second channel row being interposed between first channel rows.

10. The spinal implant of claim 9, wherein a second plurality of enlarged orifices is defined through the other of the top or bottom surfaces.

11. The spinal implant of claim 10, wherein an enlarged orifice of the second plurality of enlarged orifices includes a diameter that is different than a diameter of an enlarged orifice of the first plurality of enlarged orifices.

12. The spinal implant of claim 11, wherein an enlarged orifice of the first plurality of enlarged orifices or an enlarged orifice of the second plurality of enlarged orifices includes a circular cross-section.

13. The spinal implant of claim 12, wherein an enlarged orifice of the first plurality of enlarged orifices includes a diamond-shaped cross-section.

14. The spinal implant of claim 12, wherein an enlarged orifice of the second plurality of enlarged orifices includes a diamond-shaped cross-section.

15. The spinal implant of claim 12, wherein each enlarged orifice of the first and second pluralities of enlarged orifices includes a diamond-shaped cross-section.

16. The spinal implant of claim 9, wherein one of the third orifices includes a cross-section different than one of the first orifices or one of the second orifices.

17. The spinal implant of claim 9, wherein opposed openings of one of the third orifices are offset with respect to each other.

18. The spinal implant of claim 17, wherein a third plurality of enlarged orifices is defined through one of the opposed side surfaces.

19. The spinal implant of claim 18, wherein one enlarged orifice of the third plurality of enlarged orifices includes a diamond-shaped cross-section.

20. The spinal implant of claim 9, wherein one of the third orifices includes a diamond-shaped cross-section.

* * * * *